United States Patent
Sohn et al.

(10) Patent No.: US 10,118,974 B2
(45) Date of Patent: Nov. 6, 2018

(54) MODIFIED CONJUGATED DIENE POLYMER, A MODIFIED RUBBER COMPOSITION CONTAINING SAME, AND METHOD FOR PREPARING MODIFIED CONJUGATED DIENE POLYMER

(71) Applicant: LG Chem, Ltd., Seoul (KR)

(72) Inventors: Hae-Sung Sohn, Daejeon (KR); No-Ma Kim, Daejeon (KR); He-Seung Lee, Daejeon (KR)

(73) Assignee: LG Chem, Ltd. (KR)

( * ) Notice: Subject to any disclaimer, the term of this patent is extended or adjusted under 35 U.S.C. 154(b) by 281 days.

(21) Appl. No.: 15/121,804

(22) PCT Filed: Nov. 3, 2015

(86) PCT No.: PCT/KR2015/011719
§ 371 (c)(1),
(2) Date: Aug. 26, 2016

(87) PCT Pub. No.: WO2016/093496
PCT Pub. Date: Jun. 16, 2016

(65) Prior Publication Data
US 2017/0022298 A1 Jan. 26, 2017

(30) Foreign Application Priority Data

Dec. 11, 2014 (KR) .................. 10-2014-0178302
Oct. 14, 2015 (KR) .................. 10-2015-0143460

(51) Int. Cl.
| C08C 19/44 | (2006.01) |
| C08F 36/04 | (2006.01) |
| C08C 19/22 | (2006.01) |
| C08C 19/25 | (2006.01) |
| C08C 19/26 | (2006.01) |
| C08L 15/00 | (2006.01) |
| B60C 1/00 | (2006.01) |
| C07F 7/18 | (2006.01) |
| C08K 3/36 | (2006.01) |

(52) U.S. Cl.
CPC ............ *C08C 19/44* (2013.01); *B60C 1/0016* (2013.01); *C07F 7/1868* (2013.01); *C08C 19/22* (2013.01); *C08C 19/25* (2013.01); *C08C 19/26* (2013.01); *C08F 36/04* (2013.01); *C08K 3/36* (2013.01); *C08L 15/00* (2013.01); *Y02T 10/862* (2013.01)

(58) Field of Classification Search
CPC ........................................................ C08C 19/44
USPC ........................................................ 523/155
See application file for complete search history.

(56) References Cited

U.S. PATENT DOCUMENTS

| 2009/0163668 | A1 | 6/2009 | Yamada et al. |
| 2012/0270997 | A1 | 10/2012 | Tanaka et al. |
| 2012/0277369 | A1* | 11/2012 | Yoshida .................. C08C 19/44 524/575 |
| 2013/0172481 | A1 | 7/2013 | Okada et al. |
| 2014/0221563 | A1 | 8/2014 | Morita et al. |
| 2014/0357784 | A1 | 12/2014 | Morita et al. |
| 2016/0009903 | A1 | 1/2016 | Morita et al. |

FOREIGN PATENT DOCUMENTS

| CN | 101268107 A | 9/2008 |
| CN | 103534280 A | 1/2014 |
| EP | 2338919 A1 | 6/2011 |
| EP | 2484701 A1 | 8/2012 |
| EP | 2752433 A1 | 7/2014 |
| JP | 2013010817 A | 1/2013 |
| JP | 2013082841 A | 5/2013 |
| JP | 2013139491 A | 7/2013 |
| JP | 5535877 B2 | 7/2014 |
| JP | 2014177517 A | 9/2014 |
| JP | 2014177519 A | 9/2014 |
| KR | 101413791 B1 | 6/2014 |
| WO | 2011040312 A1 | 4/2011 |
| WO | 2014133096 A1 | 9/2014 |

OTHER PUBLICATIONS

Voronkov, Hypervalent silicon-containing organosilicon derivatives of nitrogen heterocycles, (2007), Russ. Chem. Rev. 76 825.*
Extended European Search Report for Application No. 15868082.7 dated Jan. 11, 2017.
Chinese Search Report for Application No. 2015800113977 dated Jan. 2, 2018.
Lukevics et al., "Nitrogen-containing organosilicon compounds. LXXIX. Triethoxy-and aminotriethoxy derivatives of piperazinylalkysilanes", 1978 (Abstract Only).
International Search Report from PCT/KR2015/011719, dated Feb. 17, 2016.

* cited by examiner

*Primary Examiner* — Doris L Lee
(74) *Attorney, Agent, or Firm* — Lerner, David, Littenberg, Krumholz & Mentlik, LLP

(57) ABSTRACT

Disclosed are a modified conjugated diene-based polymer represented by a specific Chemical Formula and a method of preparing the same.

14 Claims, No Drawings

MODIFIED CONJUGATED DIENE POLYMER, A MODIFIED RUBBER COMPOSITION CONTAINING SAME, AND METHOD FOR PREPARING MODIFIED CONJUGATED DIENE POLYMER

CROSS-REFERENCE TO RELATED APPLICATION

This application is a national phase entry under 35 U.S.C. § 371 of International Application No. PCT/KR2015/011719, filed Nov. 3, 2015, which claims priority to Korean Patent Application No. 10-2015-0143460, filed Oct. 14, 2015 and Korean Patent Application No. 10-2014-0178302, filed Dec. 11, 2014, the disclosures of which are incorporated herein by reference.

TECHNICAL FIELD

The present invention relates to a method of preparing a modified conjugated diene-based polymer and, more particularly, to a method of preparing a modified conjugated diene-based polymer having superior tensile strength, wear resistance, and wet skid resistance, as well as low rolling resistance, a modified conjugated diene-based polymer prepared by the method, and a rubber composition comprising the modified conjugated diene-based polymer.

BACKGROUND ART

Recently, in the vehicle industry, the demand for the durability, stability and fuel economy of vehicles is continuously increasing, and much effort is directed to satisfying the demand.

In particular, many attempts have been made to enhance the properties of rubber, as a material for vehicle tires, especially tire treads, which are in contact with roads. The rubber composition for a vehicle tire contains a conjugated diene-based polymer, such as polybutadiene or butadiene-styrene copolymer.

Thorough research is currently ongoing into the addition of various reinforcing agents to conjugated diene-based rubber compositions to increase the performance of vehicle tires. Specifically, as vehicles are required to exhibit stability, durability and fuel economy, rubber having high wet skid resistance and mechanical strength and low rolling resistance is being developed as material for vehicle tires, especially tire treads, which are in contact with roads.

In this regard, rubber compositions having superior fuel economy and wet grip are under study, as disclosed in Japanese Patent Application Publication No. 2013-139491, but the effects thereof are still insufficient.

DISCLOSURE

Technical Problem

Accordingly, the present invention has been made keeping in mind the above problems encountered in the related art, and an object of the present invention is to provide a method of preparing a modified conjugated diene-based polymer having superior tensile strength, wear resistance and wet skid resistance, as well as low rolling resistance.

Technical Solution

In order to accomplish the above object, the present invention provides a method of preparing a modified conjugated diene-based polymer, comprising: a) polymerizing a conjugated diene monomer or a conjugated diene monomer and an aromatic vinyl monomer using a hydrocarbon solvent in the presence of an organo-alkali metal compound, thus forming an active polymer having an alkali metal end; and b) coupling or linking the active polymer having the alkali metal end with a compound represented by Chemical Formula 1 below, yielding a modified conjugated diene-based polymer represented by Chemical Formula 2 below:

[Chemical Formula 1]

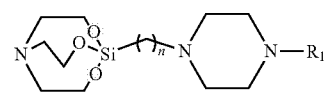

wherein $R_1$ is

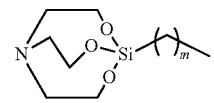

or a C1-C50 alkyl group, n is 1 to 20, and m is 0 to 20; and

[Chemical Formula 2]

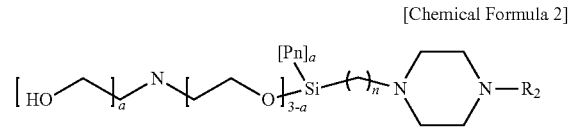

wherein $R_2$ is

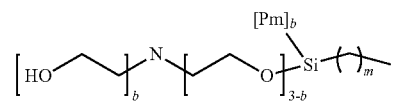

or a C1-C50 alkyl group, Pn and Pm are polymers comprising a conjugated diene monomer and a conjugated aromatic monomer as main components, with a number average molecular weight of 1,000 to 10,000,000 g/mol, and including an acryl, amine, ether or thioether monomer, Pn and Pm are identical to or different from each other, a is 1 to 3, b is 0 to 3, n is 1 to 20, and m is 0 to 20.

In addition, the present invention provides a modified conjugated diene-based polymer represented by Chemical Formula 2 below:

[Chemical Formula 2]

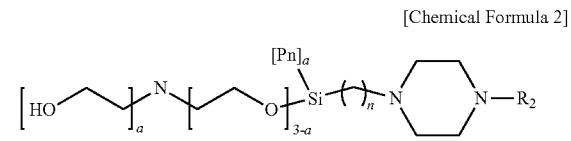

wherein $R_2$ is

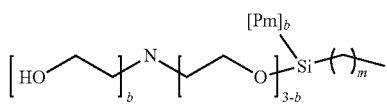

or a C1-C50 alkyl group, Pn and Pm are polymers comprising a conjugated diene monomer and a conjugated aromatic monomer as main components, with a number average molecular weight of 1,000 to 10,000,000 g/mol, and including an acryl, amine, ether or thioether monomer, Pn and Pm are identical to or different from each other, a is 1 to 3, b is 0 to 3, n is 1 to 20, and m is 0 to 20.

In addition, the present invention provides a modifier, which is a compound represented by Chemical Formula 1 below:

[Chemical Formula 1]

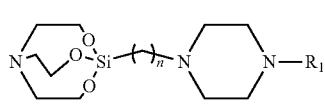

wherein $R_1$ is

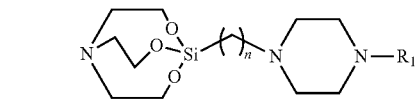

or a C1-C50 alkyl group, n is 1 to 20, and m is 0 to 20.

In addition, the present invention provides a modified conjugated diene-based polymer rubber composition, comprising the modified conjugated diene-based polymer.

In addition, the present invention provides a tire or tire tread, comprising the modified conjugated diene-based polymer rubber composition.

Advantageous Effects

According to the present invention, a modified conjugated diene-based polymer having superior tensile strength, wear resistance and wet skid resistance, as well as low rolling resistance, can be prepared, and can be utilized to produce a rubber composition for a tire.

BEST MODE

Hereinafter, a detailed description will be given of the present invention.

The present invention addresses a method of preparing a modified conjugated diene-based polymer, comprising: a) polymerizing a conjugated diene monomer or a conjugated diene monomer and an aromatic vinyl monomer using a hydrocarbon solvent in the presence of an organo-alkali metal compound, thus forming an active polymer having an alkali metal end; and b) coupling or linking the active polymer having the alkali metal end with a compound represented by Chemical Formula 1 below, yielding a modified conjugated diene-based polymer represented by Chemical Formula 2 below:

[Chemical Formula 1]

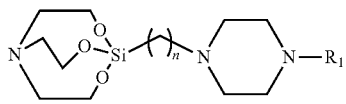

wherein $R_1$ is

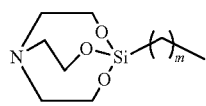

or a C1-C50 alkyl group, n is 1 to 20, and m is 0 to 20; and

[Chemical Formula 2]

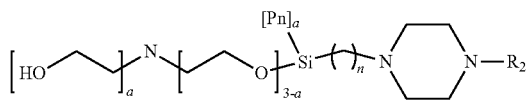

wherein $R_2$ is

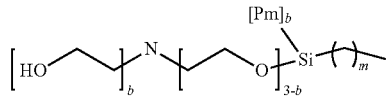

or a C1-C50 alkyl group, Pn and Pm are polymers comprising a conjugated diene monomer and a conjugated aromatic monomer as main components, with a number average molecular weight of 1,000 to 10,000,000 g/mol, and including an acryl, amine, ether or thioether monomer, Pn and Pm are identical to or different from each other, a is 1 to 3, b is 0 to 3, n is 1 to 20, and m is 0 to 20.

The organo-alkali metal compound is preferably an organolithium compound as an anionic polymerization initiator.

The organolithium may include at least one selected from the group consisting of methyllithium, ethyllithium, isopropyllithium, n-butyllithium, sec-butyllithium, tert-butyllithium, n-decyllithium, tert-octyllithium, phenyllithium, 1-naphthyllithium, n-eicosyllithium, 4-butylphenyllithium, 4-tolyllithium, cyclohexyllithium, 3,5-di-n-heptylcyclohexyllithium, and 4-cyclopentyllithium.

The organo-alkali metal compound may be used in an amount of 0.01 to 10 mmol, 0.05 to 5 mmol, 0.3 to 5 mmol, 0.1 to 2 mmol, or 0.15 to 0.8 mmol, based on 100 g in total of the monomer.

The molar ratio of the organo-alkali metal compound and the compound represented by Chemical Formula 1, the compound represented by Chemical Formula 2, or the polymer, may range from 1:0.1 to 1:10, or 1:0.5 to 1:2.

In the present invention, the conjugated diene monomer may include, but is not necessarily limited to, at least one selected from the group consisting of 1,3-butadiene, 2,3-dimethyl-1,3-butadiene, piperylene, 3-butyl-1,3-octadiene, isoprene, and 2-phenyl-1,3-butadiene.

The conjugated diene monomer may be used in an amount of 60 to 100 wt %, preferably 60 to 85 wt %, and more preferably 60 to 80 wt %, based on 100 wt % in total of the conjugated diene monomer and the aromatic vinyl monomer. When the conjugated diene monomer is used in an amount of 100 wt % based on 100 wt % in total of the conjugated diene monomer and the aromatic vinyl monomer, an active polymer, resulting from polymerizing the conjugated diene monomer alone, without the aromatic vinyl monomer, is provided.

In the present invention, the aromatic vinyl monomer may include at least one selected from the group consisting of styrene, α-methylstyrene, 3-methylstyrene, 4-methylstyrene, 4-propylstyrene, 1-vinylnaphthalene, 4-cyclohexylstyrene, 4-(p-methylphenyl)styrene, and 1-vinyl-5-hexylnaphthalene. Preferably useful is styrene or α-methylstyrene.

The aromatic vinyl monomer may be used in an amount of 0 to 40 wt %, preferably 15 to 40 wt %, and more preferably 20 to 40 wt %, based on 100 wt % in total of the conjugated diene monomer and the aromatic vinyl monomer. When the vinyl aromatic monomer is used in an amount of 0 wt % based on 100 wt % in total of the conjugated diene monomer and the aromatic vinyl monomer, an active polymer, resulting from polymerizing the conjugated diene monomer alone, without the aromatic vinyl monomer, is provided.

In the polymer, an acryl, amine, ether, thioether or silane monomer may be contained in a small amount, for example, in an amount of 0 to 10 wt %, and preferably 0 to 1 wt %, based on 100 wt % in total of the monomer.

The hydrocarbon solvent may be exemplified by a hydrocarbon, or may include, but is not necessarily limited to, at least one selected from the group consisting of n-pentane, n-hexane, n-heptane, isooctane, cyclohexane, toluene, benzene, and xylene.

In a), the polymerization may be exemplified by anionic polymerization.

Specifically, the polymerization in a) may be living anionic polymerization in which an active end is obtained through a growth reaction involving anions.

Also, the polymerization in a) may be either high-temperature polymerization or room-temperature polymerization.

High-temperature polymerization is a polymerization process that comprises adding the organometallic compound and then applying heat to increase the reaction temperature, and room-temperature polymerization is a polymerization process that takes place in such a way that heat is not applied after the organometallic compound is added.

The polymerization in a) may take place at a temperature ranging from −20 to 200° C., preferably 0 to 150° C., and more preferably 10 to 120° C.

As used herein, the active polymer having an alkali metal end refers to a polymer comprising a polymer anion and an alkali metal cation, which are coupled with each other.

In the method of preparing the modified conjugated diene-based polymer according to the present invention, the polymerizing in a) may be performed with the additional use of a polar additive.

The polar additive may be a base, or may include ether, amine or mixtures thereof. Specifically, it may be selected from the group consisting of tetrahydrofuran, ditetrahydrofurylpropane, diethylether, cycloamylether, dipropylether, ethylenedimethylether, ethylenedimethylether, diethyleneglycol, dimethylether, tert-butoxyethoxyethane bis(2-dimethylaminoethyl)ether, (dimethylaminoethyl)ethylether, trimethylamine, triethylamine, tripropyl amine, and tetramethylethylenediamine Preferably useful is ditetrahydropropylpropane, triethylamine, or tetramethylethylenediamine.

The polar additive may be used in an amount of 0.001 to 50 g, preferably 0.001 to 10 g, and more preferably 0.005 to 1 g, based on 100 g in total of the added monomer.

The polar additive may be used in an amount of 0.001 to 10 g, preferably 0.005 to 1 g, and more preferably 0.005 to 0.1 g, based on 1 mmol in total of the added organo-alkali metal compound.

When the conjugated diene monomer and the aromatic vinyl monomer are copolymerized, a block copolymer may be easily prepared due to the difference in the reaction rates therebetween. However, when the polar additive is added, the low reaction rate of the vinyl aromatic compound may be increased to thus obtain the microstructure of the corresponding copolymer, for example, a random copolymer.

In b), the active polymer having the alkali metal end obtained in a) is coupled or linked with the compound represented by Chemical Formula 1 below:

[Chemical Formula 1]

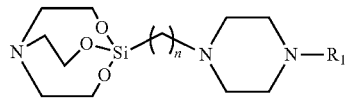

wherein R₁ is

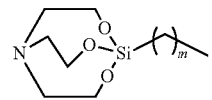

or a C1-C50 alkyl group, n is 1 to 20, and m is 0 to 20.

Preferably, the compound represented by Chemical Formula 1 is the compound represented by Chemical Formula 1a below.

[Chemical Formula 1a]

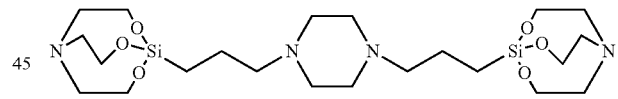

The compound represented by Chemical Formula 1 is used in an amount of 0.01 to 10 mmol, preferably 0.05 to 5 mmol, and more preferably 0.1 to 2 mmol, based on 100 g in total of the monomer.

In b), prepared is a modified conjugated diene-based polymer in which the compound represented by Chemical Formula 1 is bound to the end of the chain of the active polymer having the alkali metal end.

The modified conjugated diene-based polymer is the compound represented by Chemical Formula 2 below:

[Chemical Formula 2]

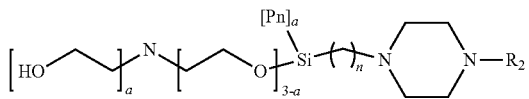

wherein $R_2$ is

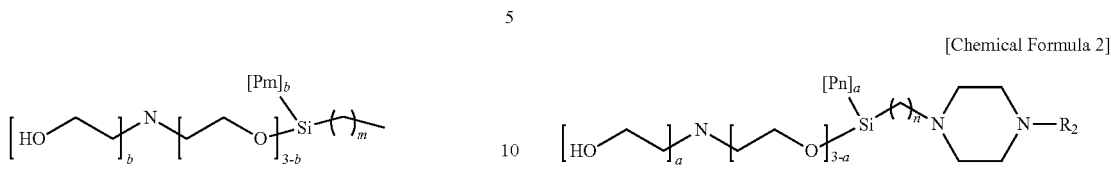

or a C1-C50 alkyl group, Pn and Pm are polymers comprising a conjugated diene monomer and a conjugated aromatic monomer as main components, with a number average molecular weight of 1,000 to 10,000,000 g/mol, and including an acryl, amine, ether or thioether monomer, Pn and Pm are identical to or different from each other, a is 1 to 3, b is 0 to 3, n is 1 to 20, and m is 0 to 20.

The compound represented by Chemical Formula 2 is a conjugated diene-based polymer using the compound represented by Chemical Formula 1, in which at least one conjugated diene-based polymer end is linked with the silane group of Chemical Formula 1.

Preferably, the compound represented by Chemical Formula 2 is the compound represented by Chemical Formula 2a below:

[Chemical Formula 2a]

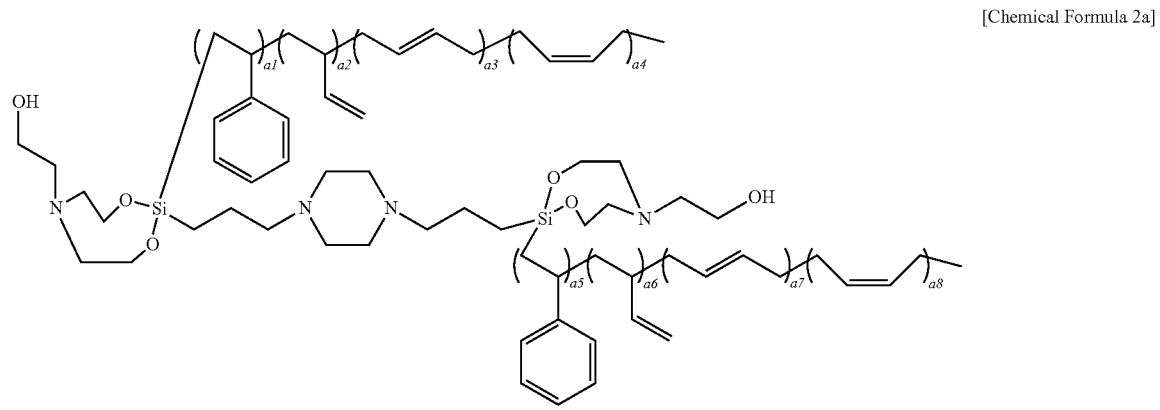

wherein a1 to a8 each range from 10 to 100,000.

Also, b) is performed at 0 to 90° C. for 1 mm to 5 hr.

The method of preparing the modified conjugated diene-based polymer according to the present invention may be carried out in a batch manner, or alternatively in a continuous manner using a single reactor or two or more reactors.

In addition, the present invention addresses a modified conjugated diene-based polymer represented by Chemical Formula 2 below:

[Chemical Formula 2]

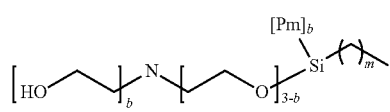

wherein $R_2$ is or a C1-C50 alkyl group, Pn and Pm are polymers comprising a conjugated diene monomer and a conjugated aromatic monomer as main components, with a number average molecular weight of 1,000 to 10,000,000 g/mol, and including an acryl, amine, ether or thioether monomer, Pn and Pm are identical to or different from each other, a is 1 to 3, b is 0 to 3, n is 1 to 20, and m is 0 to 20.

The modified conjugated diene-based polymer represented by Chemical Formula 2 may be the modified conjugated diene-based polymer represented by Chemical Formula 2a below.

[Chemical Formula 2a]

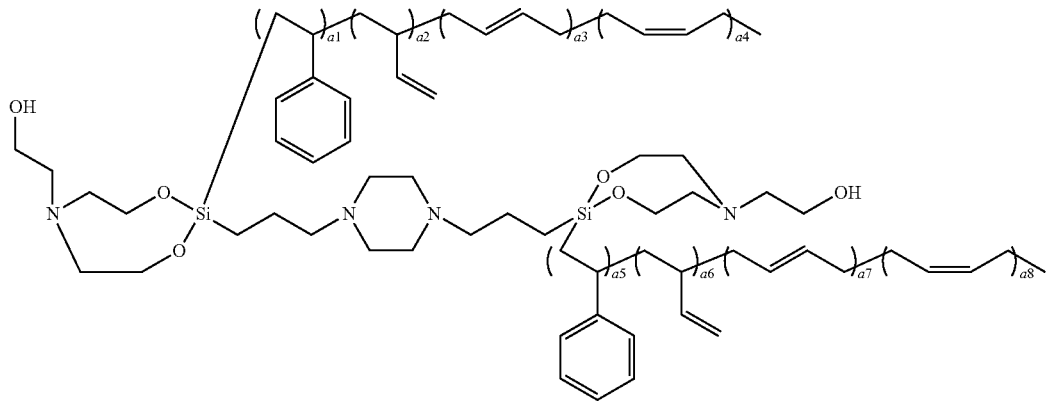

wherein a1 to a8 each range from 10 to 100,000.

The modified conjugated diene-based polymer may be a chain composed exclusively of a conjugated diene monomer or composed of a conjugated diene monomer and an aromatic vinyl monomer.

The chain composed of a conjugated diene monomer and an aromatic vinyl monomer may be a polymer chain comprising the aromatic vinyl monomer in an amount of 0.0001 to 40 wt %, preferably 10 to 35 wt %, and more preferably 20 to 30 wt %, based on 100 wt % in total of the conjugated diene monomer and the aromatic vinyl monomer.

The polymer chain comprising the conjugated diene monomer and the aromatic vinyl monomer may be, for example, a random polymer chain.

The modified conjugated diene-based polymer may have a Mooney viscosity of 20 or more, preferably from 20 to 150, and more preferably from 40 to 100.

The modified conjugated diene-based polymer may have a number average molecular weight of 1,000 to 10,000,000 g/mol, preferably 10,000 to 1,000,000 g/mol, and more preferably 100,000 to 500,000 g/mol.

The modified conjugated diene-based polymer has a vinyl content of 10 wt % or more, preferably 25 wt % or more, and more preferably 30 to 70 wt %. Given the above vinyl content range, the glass transition temperature of the polymer may be elevated. Thus, when such a polymer is applied to tires, the properties required of tires, such as running resistance and wet grip, may be satisfied, and superior fuel economy may result.

The vinyl content refers to the amount of a monomer having a vinyl group, or the amount not of 1,4-added conjugated diene monomer but of 1,2-added conjugated diene monomer, based on 100 wt % of the conjugated diene monomer.

The modified conjugated diene-based polymer has a polydispersity index (PDI) of 1 to 10, preferably 1 to 5, and more preferably 1 to 3.

The modified conjugated diene-based polymer may exhibit viscoelastic properties. When measured at 10 Hz using DMA after mixing with silica, Tan δ at 0° C. may be in the range of 0.6 to 1 or 0.9 to 1. Given the above Tan δ range, desired skid resistance or wet resistance may be obtained.

Also, Tan δ at 60° C. may be in the range of 0.06 to 0.09 or 0.07 to 0.08. Given the above Tan δ range, desired rolling resistance or rotational resistance (RR) may be obtained.

In addition, the present invention addresses a modifier, which is a compound represented by Chemical Formula 1 below:

[Chemical Formula 1]

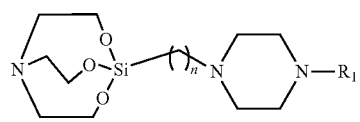

wherein $R_1$ is

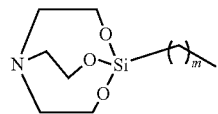

or a C1-C50 alkyl group, n is 1 to 20, and m is 0 to 20.

The modifier, which is the compound represented by Chemical Formula 1, may be the modifier represented by Chemical Formula 1a below.

[Chemical Formula 1a]

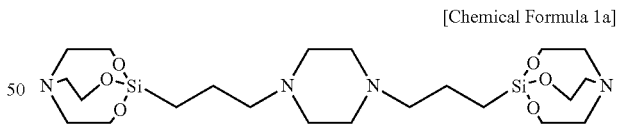

In addition, the present invention addresses a modified conjugated diene-based polymer rubber composition, including the modified conjugated diene-based polymer prepared by the method as described above.

The modified conjugated diene-based polymer rubber composition according to the present invention comprises 10 to 100 parts by weight of the modified conjugated diene-based polymer and 0.1 to 200 parts by weight of an inorganic filler based on 100 parts by weight of the modified conjugated diene-based polymer.

The amount of the inorganic filler may be 10 to 150 parts by weight, or 50 to 100 parts by weight.

The inorganic filler may include carbon black, silica, or a mixture thereof.

The inorganic filler may be silica. As such, dispersibility is significantly increased, and the end of the modified conjugated diene-based polymer of the invention may be coupled (sealed) with silica particles, thus significantly decreasing hysteresis loss.

The modified conjugated diene-based polymer rubber composition may further comprise an additional conjugated diene-based polymer.

Examples of the additional conjugated diene-based polymer may include SBR (styrene-butadiene rubber), BR (butadiene rubber), natural rubber, and mixtures thereof.

SBR may be exemplified by SSBR (solution styrene-butadiene rubber).

The modified conjugated diene-based polymer rubber composition according to the present invention may comprise 20 to 100 parts by weight of the modified conjugated diene-based polymer and 0 to 80 parts by weight of the additional conjugated diene-based polymer.

Alternatively, the modified conjugated diene-based polymer rubber composition according to the present invention may comprise 20 to 99 parts by weight of the modified conjugated diene-based polymer and 1 to 80 parts by weight of the additional conjugated diene-based polymer.

Alternatively, the modified conjugated diene-based polymer rubber composition according to the present invention may comprise 10 to 100 parts by weight of the modified conjugated diene-based polymer, 0 to 90 parts by weight of the additional conjugated diene-based polymer, 0 to 100 parts by weight of carbon black, 5 to 200 parts by weight of silica, and 2 to 20 parts by weight of a silane coupling agent.

Alternatively, the modified conjugated diene-based polymer rubber composition according to the present invention may comprise 10 to 100 parts by weight of the modified conjugated diene-based polymer, 0 to 90 parts by weight of the additional conjugated diene-based polymer, 0 to 100 parts by weight of carbon black, 5 to 200 parts by weight of silica, and 2 to 20 parts by weight of a silane coupling agent, in which the total weight of the modified conjugated diene-based polymer and the additional conjugated diene-based polymer may be 100 parts by weight.

Alternatively, the modified conjugated diene-based polymer rubber composition according to the present invention may comprise 100 parts by weight of a polymer mixture comprising 10 to 99 wt % of the modified conjugated diene-based polymer and 1 to 90 wt % of the additional conjugated diene-based polymer, 1 to 100 parts by weight of carbon black, 5 to 200 parts by weight of silica, and 2 to 20 parts by weight of a silane coupling agent.

Also, the modified conjugated diene-based polymer rubber composition may further comprise 1 to 100 parts by weight of oil.

The oil may be exemplified by mineral oil or a softener.

The oil may be used in an amount of, for example, 10 to 100 parts by weight, or 20 to 80 parts by weight, based on 100 parts by weight of the conjugated diene-based polymer. Given the above oil content range, desired properties may be exhibited, and the rubber composition may be appropriately softened, thus increasing processability.

In addition, the present invention addresses a tire or tire tread, comprising the modified conjugated diene-based polymer rubber composition.

The tire or tire tread is manufactured using the rubber composition including the modified conjugated diene-based polymer, which has high compatibility with an inorganic filler and improved processability, thereby exhibiting superior tensile strength, wear resistance and wet skid resistance and low rolling resistance.

MODE FOR INVENTION

A better understanding of the present invention may be obtained via the following examples, which are merely set forth to illustrate the present invention, and those skilled in the art will appreciate that various changes and modifications are possible, without departing from the scope and spirit of the invention as disclosed in the accompanying claims.

EXAMPLES

Example 1

A continuous reactor comprising 8 L, 8 L, 16 L and 16 L autoclave reactors connected in series was prepared. A 60 wt % styrene solution at 344 g/h, a 60 wt % 1,3-butadiene solution at 860 g/h, n-hexane at 3550 g/h, a 3 wt % ethyl(tetrahydrofurfuryl)ether solution as a polar additive at 33.7 g/h, and a 1 wt % n-butyllithium solution as an initiator at 36.0 g/h were fed into the first reactor of the continuous reactor. The temperature of the first reactor was maintained at 55° C., and the retention time was set to 10 mm. The polymer was transferred from the first reactor into the second reactor using a gear pump, the temperature of the second reactor was maintained at 58° C., and the retention time was set to 10 mm. The polymer was transferred from the second reactor into the third reactor using a gear pump, and a 60 wt % 1,3-butadiene solution was additionally fed at a rate of 45.3 g/h. The temperature of the third reactor was maintained at 70° C., and the retention time was set to 40 min The polymer was transferred from the third reactor into the fourth reactor using a gear pump, and a solution of N,N'-bis(3-trioxaazasilabicycloundecylpropyl)piperazine, diluted to 3 wt % in n-hexane, was fed at a rate of 25.0 g/h as a modifier. The temperature of the fourth reactor was maintained at 65° C., and the retention time was set to 30 mm. The polymer solution output from the fourth reactor was added with a 20 wt % Wingstay solution in n-hexane at 18.8 g/h as a polymerization stopper to stop the polymerization reaction. The resulting polymer was added to water warmed with steam, stirred to remove the solvent, and then roll dried to remove the remaining solvent and water, yielding a modified conjugated diene-based polymer A.

Example 2

A modified conjugated diene-based polymer B was prepared in the same manner as in Example 1, with the exception that the solution of 3 wt % N,N'-bis(3-trioxaazasilabicycloundecylpropyl)piperazine in n-hexane was fed at a rate of 38.8 g/h as the modifier.

Example 3

A modified conjugated diene-based polymer C was prepared in the same manner as in Example 1, with the exception that the solution of 3 wt % N-(3-trioxaazasilabicycloundecylpropyl)-N'-propylpiperazine in n-hexane was fed at a rate of 15.0 g/h as the modifier.

Example 4

A modified conjugated diene-based polymer D was prepared in the same manner as in Example 1, with the exception that the solution of 3 wt % N-(3-trioxaazasilabicycloundecylpropyl)-N'-propylpiperazine in n-hexane was fed at a rate of 30.0 g/h as the modifier.

Comparative Example 1

An unmodified conjugated diene-based polymer E was prepared in the same manner as in Example 1, with the exception that tetrachlorosilane, diluted to 0.5 wt % in n-hexane, was fed at a rate of 25.5 g/h, in lieu of the modifier.

Comparative Example 2

A continuous reactor comprising 8 L, 8 L, and 16 L autoclave reactors connected in series was prepared. A 60 wt % styrene solution at 344 g/h, a 60 wt % 1,3-butadiene solution at 860 g/h, n-hexane at 3550 g/h, a 3 wt % ethyl(tetrahydrofurfuryl)ether solution as a polar additive at 31.5 g/h, and a 1 wt % n-butyllithium solution as an initiator at 29.3 g/h were fed into the first reactor of the continuous reactor. The temperature of the first reactor was maintained at 55° C., and the retention time was set to 10 min. The polymer was transferred from the first reactor into the second reactor using a gear pump, the temperature of the second reactor was maintained at 58° C., and the retention time was set to 10 min. The polymer was transferred from the second reactor into the third reactor using a gear pump, and a 60 wt % 1,3-butadiene solution was additionally fed at a rate of 45.3 g/h. The temperature of the second reactor was maintained at 70° C., and the retention time was set to 40 min. The polymer solution output from the third reactor was added with a Wingstay solution as a polymerization stopper to stop the polymerization reaction. The resulting polymer was added to water warmed with steam, stirred to remove the solvent, and then roll dried to remove the remaining solvent and water, yielding a modified conjugated diene-based polymer F.

The conjugated diene-based polymers of Examples 1 to 4 and Comparative Examples 1 and 2 were analyzed through the following methods. The results are shown in Table 1 below.

a) Mooney viscosity: two samples having a weight of 15 g or more were preheated for 1 min and then measured at 100° C. for 4 min using an MV-2000, made by ALPHA Technologies.

b) Styrene monomer (SM) and Vinyl content: measurement was conducted using NMR.

c) Weight average molecular weight (Mw), Number average molecular weight (Mn), and Polydispersity Index (PDI): measurement was conducted via GPC at 40° C. The column used herein was a combination of two PLgel Olexis columns and one PLgel mixed-C column, made by Polymer Laboratories, and all of the replaced columns were mixed bed-type columns.

Also, polystyrene (PS) was the GPC standard material for the calculation of molecular weight.

TABLE 1

|  |  | Ex. 1 | Ex. 2 | Ex. 3 | Ex. 4 | C. Ex. 1 | C. Ex. 2 |
|---|---|---|---|---|---|---|---|
| Sample |  | 1<br>A | 2<br>B | 3<br>C | 4<br>D | 5<br>E | 6<br>F |
| Mooney viscosity (100° C.) |  | 75 | 76 | 78 | 66 | 74 | 72 |

TABLE 1-continued

|  |  | Ex. 1 | Ex. 2 | Ex. 3 | Ex. 4 | C. Ex. 1 | C. Ex. 2 |
|---|---|---|---|---|---|---|---|
| NMR | SM (%) | 27.2 | 27.5 | 27.4 | 27.7 | 27.3 | 26.8 |
|  | Vinyl (%) | 42.5 | 42.3 | 42.3 | 42.6 | 43.0 | 43.3 |
| GPC | Mn (×10$^4$) | 29 | 31 | 32 | 30 | 28 | 31 |
|  | Mw (×10$^4$) | 53 | 54 | 54 | 48 | 54 | 50 |
|  | PDI | 1.8 | 1.7 | 1.7 | 1.6 | 1.9 | 1.6 |

Preparation Examples 1 to 6

Preparation of Rubber Composition

The conjugated diene-based polymer rubber compositions were prepared using samples A to F shown in Table 1, as raw rubber, under the mixing conditions shown in Table 2 below.

TABLE 2

| unit: parts by weight | Preparation Examples 1 to 6 |
|---|---|
| Rubber used | Examples 1 to 6 |
| Rubber | 100.0 |
| Silica | 70.0 |
| Coupling agent | 11.2 |
| Processing oil | 37.5 |
| Zinc oxide | 3.0 |
| Stearic acid | 2.0 |
| Antioxidant | 2.0 |
| Anti-aging agent | 2.0 |
| Wax | 1.0 |
| Rubber accelerator | 1.75 |
| Sulfur | 1.5 |
| Vulcanization accelerator | 2.0 |
| Total weight | 233.95 |

The conjugated diene-based polymer rubber composition was kneaded as follows. Specifically, upon primary kneading, raw rubber (conjugated diene-based polymer), a filler, an organosilane coupling agent, oil, zinc oxide, a stearic acid antioxidant, an anti-aging agent, wax and an accelerator were kneaded at 80 rpm using a Banbury mixer provided with a temperature controller. For this, the temperature of the kneader was controlled, and a first mixture was obtained at a discharge temperature of 140 to 150° C. Upon secondary kneading, the first mixture was cooled to room temperature, after which rubber, sulfur and a vulcanization accelerator were placed in the kneader, and a second mixture was obtained at a discharge temperature of 45 to 60° C. Upon tertiary kneading, the second mixture was molded and vulcanized at 180° C. for T90+10 mm using a vulcanization press, thereby manufacturing vulcanized rubber.

The properties of the manufactured vulcanized rubber were measured through the following methods.

1) Mooney viscosity: two samples having a weight of 15 g or more were preheated for 1 min and then measured at 100° C. for 4 min using an MV-2000, made by ALPHA Technologies.

2) Payne effect: a sample having a weight of 7 g or more was measured in the strain sweep range of 0.04 to 40.0% at 60° C. at 1 Hz using an RPA 2000, made by ALPHA Technologies.

3) Tensile Testing

According to the tensile testing method of ASTM 412, the tensile strength upon cutting a test sample and tensile stress (300% modulus) at 300% elongation were measured.

4) Rolling Resistance (RR) and Wet Grip

The rolling resistance (RR) and wet grip of rubber were measured using DMTS (Dynamic mechanical thermal spectrometry; GABO, EPLEXOR 500N). The measurement conditions were as follows: frequency: 10 Hz, strain (static strain: 3%, dynamic strain: 0.25%), and temperature: −60 to 70° C. As such, RR was evaluated to be good with a decrease in Tan δ at 60° C., and wet grip was evaluated to be good with an increase in Tan δ at 0° C. These values were represented as indexes relative to the value of Comparative Example 5, which was set to 100, and were evaluated to be superior with an increase in the indexes.

TABLE 3

|  | Prep. Ex. 1 | Prep. Ex. 2 | Prep. Ex. 3 | Prep. Ex. 4 | Prep. Ex. 5 | Prep. Ex. 6 |
| --- | --- | --- | --- | --- | --- | --- |
| Sample | A | B | C | D | E | F |
| Mooney viscosity (MV) upon primary kneading | 72 | 74 | 74 | 63 | 75 | 83 |
| Mooney viscosity (MV) upon secondary kneading | 62 | 63 | 64 | 55 | 69 | 71 |
| Payne effect | 0.31 | 0.27 | 0.32 | 0.26 | 0.50 | 0.55 |
| 300% Modulus (Kgf/cm$^2$) | 105 | 102 | 102 | 104 | 100 | 102 |
| Tensile strength (Kgf/cm$^2$) | 104 | 100 | 102 | 104 | 100 | 99 |
| Tanδ at 0° C. | 108 | 112 | 106 | 110 | 100 | 95 |
| Tanδ at 60° C. | 118 | 120 | 116 | 118 | 100 | 92 |

As is apparent from the results of Table 3, the modified conjugated diene-based polymer rubber compositions of Preparation Examples 1 to 4 according to the present invention exhibited 300% modulus (tensile stress) and tensile strength equal to or superior to those of the unmodified conjugated diene-based rubber compositions of Preparation Examples 5 and 6.

In particular, Tan δ at 0° C. was improved by 6 to 12% and Tan δ at 60° C. was improved by 16 to 20%. Thus, when the modified conjugated diene-based polymer of the invention was used for a tire, high wet skid resistance and low rolling resistance resulted. Also, Preparation Examples 1 and 2 using the modified conjugated diene-based polymers A and B by the use of N,N'-bis(3-trioxaazasilabicycloundecylpropyl)piperazine manifested slightly superior results, compared to when using the modified conjugated diene-based polymers C and D by the use of N(3-trioxaazasilabicycloundecylpropyl)N'-propylpiperazine. As the amount of the modifier was increased, rolling resistance and wet grip were improved. However, the products using the modified conjugated diene-based polymer were superior in all properties, compared to when using the unmodified conjugated diene-based polymer.

The invention claimed is:

1. A modified conjugated diene-based polymer, which is a compound represented by Chemical Formula 2 below:

[Chemical Formula 2]

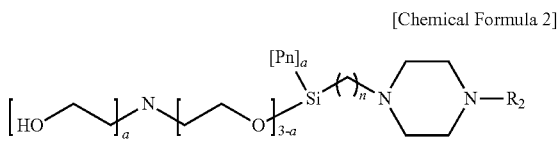

wherein R$_2$ is

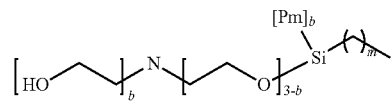

or a C1-C50 alkyl group, Pn and Pm are polymers comprising a conjugated diene monomer and a conjugated aromatic monomer as main components, with a number average molecular weight of 1,000 to 10,000,000 g/mol, and including an acryl, amine, ether or thioether monomer, Pn and Pm are identical to or different from each other, a is 1 to 3, b is 0 to 3, n is 1 to 20, and m is 0 to 20.

2. The modified conjugated diene-based polymer of claim 1, wherein the compound represented by Chemical Formula 2 is a compound represented by Chemical Formula 2a below:

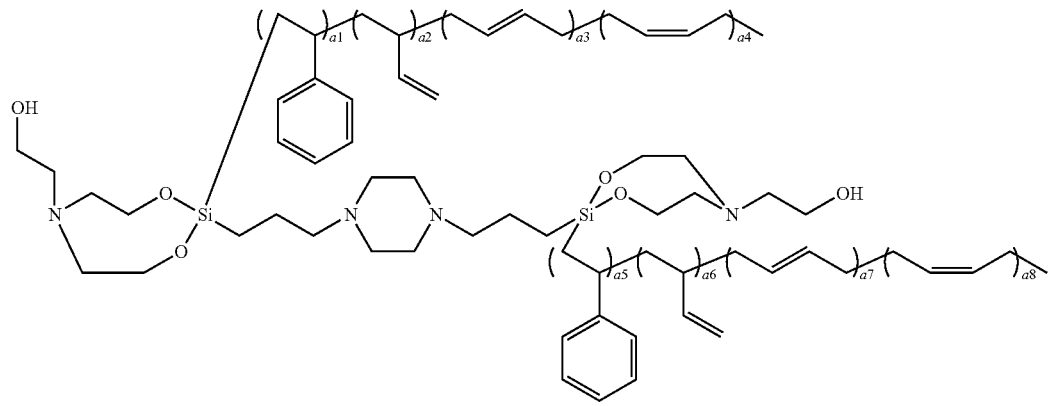

[Chemical Formula 2a]

wherein a1 to a8 each range from 10 to 100,000.

3. A method of preparing a modified conjugated diene-based polymer, comprising:
  a) polymerizing a conjugated diene monomer or a conjugated diene monomer and an aromatic vinyl monomer using a hydrocarbon solvent in presence of an organo-alkali metal compound, thus forming an active polymer having an alkali metal end; and
  b) coupling or linking the active polymer having the alkali metal end with a compound represented by Chemical Formula 1 below, yielding a modified conjugated diene-based polymer, which is a compound represented by Chemical Formula 2 below:

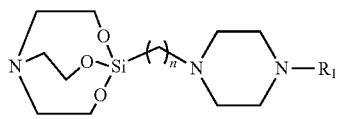

[Chemical Formula 1]

wherein $R_1$ is

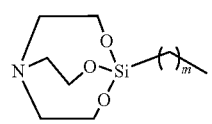

or a C1-C50 alkyl group, n is 1 to 20, and m is 0 to 20; and

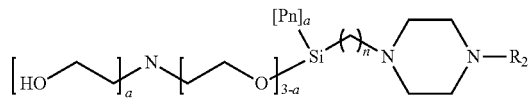

[Chemical Formula 2]

wherein $R_2$ is

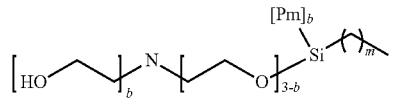

or a C1-C50 alkyl group, Pn and Pm are polymers comprising a conjugated diene monomer and a conjugated aromatic monomer as main components, with a number average molecular weight of 1,000 to 10,000,000 g/mol, and including an acryl, amine, ether or thioether monomer, Pn and Pm are identical to or different from each other, a is 1 to 3, b is 0 to 3, n is 1 to 20, and m is 0 to 20.

4. The method of claim 3, wherein the compound represented by Chemical Formula 1 is a compound represented by Chemical Formula 1a below

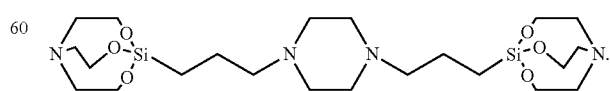

[Chemical Formula 1a]

5. The method of claim 3, wherein the compound represented by Chemical Formula 2 is a compound represented by Chemical Formula 2a below:

[Chemical Formula 2a]

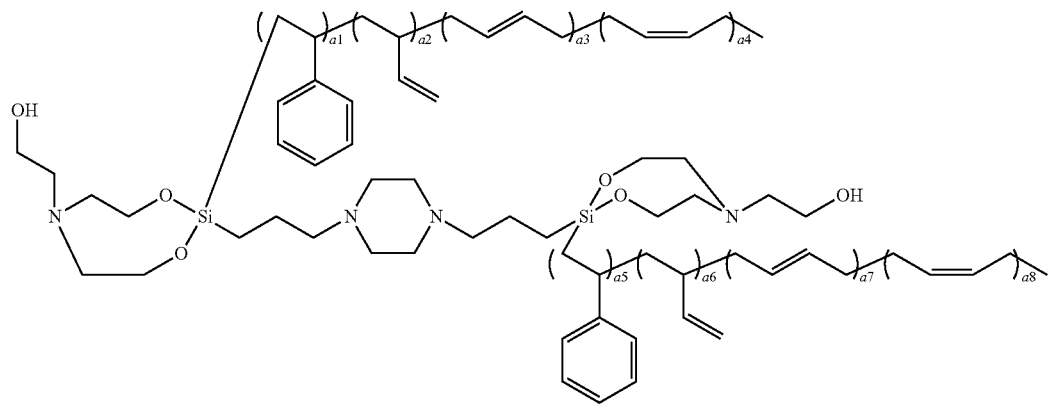

wherein a1 to a8 each range from 10 to 100,000.

6. The method of claim 3, wherein the organo-alkali metal compound is used in an amount of 0.01 to 10 mmol based on 100 g in total of the monomer.

7. The method of claim 3, wherein a molar ratio of the organo-alkali metal compound and the compound represented by Chemical Formula 1 is 1:0.1 to 1:10.

8. The method of claim 3, wherein the polymerizing in a) is performed with additional use of a polar additive.

9. The method of claim 8, wherein the polar additive is added in an amount of 0.001 to 50 g based on 1 mmol in total of the compound represented by Chemical Formula 1.

10. A modifier, which is a compound represented by Chemical Formula 1 below:

[Chemical Formula 1]

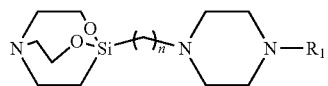

wherein $R_1$ is

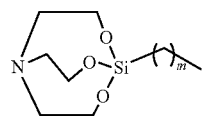

or a C1-C50 alkyl group, n is 1 to 20, and m is 0 to 20.

11. The modifier of claim 10, wherein the compound represented by Chemical Formula 1 is a compound represented by Chemical Formula 1a below

[Chemical Formula 1a]

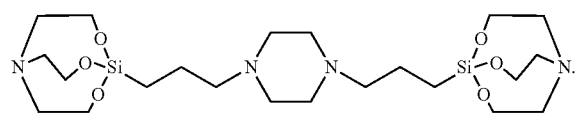

12. A modified conjugated diene-based polymer rubber composition, comprising 10 to 100 parts by weight of the modified conjugated diene-based polymer of claim 1 and 0.1 to 200 parts by weight of an inorganic filler based on 100 parts by weight of the modified conjugated diene-based polymer.

13. The modified conjugated diene-based polymer rubber composition of claim 12, wherein the inorganic filler comprises at least one of carbon black and silica.

14. A tire or tire tread, comprising the modified conjugated diene-based polymer rubber composition of claimed 12.

* * * * *